United States Patent
Drake

(10) Patent No.: US 9,512,468 B2
(45) Date of Patent: Dec. 6, 2016

(54) DETECTION METHOD USES MAGNETIC AND DETECTABLE NANOPARTICLES WITH OLIGONUCLEOTIDES ATTACHED THERETO

(71) Applicant: INDUSTRIAL TECHNOLOGY RESEARCH INSTITUTE, Chutung, Hsinchu (TW)

(72) Inventor: Philip-Leslie Drake, Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 20 days.

(21) Appl. No.: 13/670,236

(22) Filed: Nov. 6, 2012

(65) Prior Publication Data

US 2014/0127695 A1  May 8, 2014

(51) Int. Cl.
*C12Q 1/68* (2006.01)

(52) U.S. Cl.
CPC .................. *C12Q 1/6816* (2013.01)

(58) Field of Classification Search
None
See application file for complete search history.

(56) References Cited

U.S. PATENT DOCUMENTS

| | | | |
|---|---|---|---|
| 5,266,498 A | 11/1993 | Tarcha et al. | |
| 5,306,403 A | 4/1994 | Vo-Dinh | |
| 5,475,610 A * | 12/1995 | Atwood et al. | 700/269 |
| 6,127,120 A | 10/2000 | Graham et al. | |
| 6,174,677 B1 | 1/2001 | Vo-Dinh | |
| 6,361,944 B1 | 3/2002 | Mirkin et al. | |
| 6,417,340 B1 | 7/2002 | Mirkin et al. | |
| 6,495,324 B1 | 12/2002 | Mirkin et al. | |
| 6,610,491 B2 | 8/2003 | Mirkin et al. | |
| 6,673,548 B2 | 1/2004 | Mirkin et al. | |
| 6,677,122 B2 | 1/2004 | Mirkin et al. | |
| 6,682,895 B2 | 1/2004 | Mirkin et al. | |
| 6,709,825 B2 | 3/2004 | Mirkin et al. | |
| 6,720,147 B2 | 4/2004 | Mirkin et al. | |
| 6,720,411 B2 | 4/2004 | Mirkin et al. | |
| 6,730,269 B2 | 5/2004 | Mirkin et al. | |
| 6,740,491 B2 | 5/2004 | Mirkin et al. | |
| 6,750,016 B2 | 6/2004 | Mirkin et al. | |
| 6,759,199 B2 | 7/2004 | Mirkin et al. | |
| 6,767,702 B2 | 7/2004 | Mirkin et al. | |
| 6,773,884 B2 | 8/2004 | Mirkin et al. | |
| 6,777,186 B2 | 8/2004 | Mirkin et al. | |
| 6,812,334 B1 | 11/2004 | Mirkin et al. | |
| 6,818,753 B2 | 11/2004 | Mirkin et al. | |
| 6,828,432 B2 | 12/2004 | Mirkin et al. | |
| 6,861,221 B2 | 3/2005 | Mirkin et al. | |
| 6,878,814 B2 | 4/2005 | Mirkin et al. | |
| 6,902,895 B2 | 6/2005 | Mirkin et al. | |
| 6,903,207 B2 | 6/2005 | Mirkin et al. | |
| 6,962,786 B2 | 11/2005 | Mirkin et al. | |
| 6,969,761 B2 | 11/2005 | Mirkin et al. | |
| 6,974,669 B2 | 12/2005 | Mirkin et al. | |
| 6,984,491 B2 | 1/2006 | Mirkin et al. | |
| 6,986,989 B2 | 1/2006 | Mirkin et al. | |
| 7,098,320 B1 | 8/2006 | Mirkin et al. | |
| 7,115,688 B1 | 10/2006 | Mirkin et al. | |
| 7,135,055 B2 | 11/2006 | Mirkin et al. | |
| 7,147,687 B2 | 12/2006 | Mirkin et al. | |
| 7,169,556 B2 | 1/2007 | Park et al. | |
| 7,186,814 B2 | 3/2007 | Garimella et al. | |
| 7,208,587 B2 | 4/2007 | Mirkin et al. | |
| 7,238,472 B2 | 7/2007 | Mirkin et al. | |
| 7,250,499 B2 | 7/2007 | Mirkin et al. | |
| 7,259,252 B2 | 8/2007 | Mirkin et al. | |
| 7,364,857 B2 | 4/2008 | Cho et al. | |
| 7,651,839 B2 | 1/2010 | Li et al. | |
| 7,829,350 B2 | 11/2010 | Josephson et al. | |
| 7,985,539 B2 | 7/2011 | Mirkin et al. | |
| 8,062,841 B2 | 11/2011 | Su et al. | |
| 2003/0143604 A1 * | 7/2003 | Storhoff | C12Q 1/6844 435/6.11 |
| 2004/0110220 A1 | 6/2004 | Mirkin et al. | |
| 2005/0118589 A1 * | 6/2005 | Vann | B82Y 5/00 435/6.12 |
| 2008/0160634 A1 * | 7/2008 | Su et al. | 436/501 |
| 2009/0005260 A1 * | 1/2009 | Su et al. | 506/9 |
| 2010/0255599 A1 | 10/2010 | Drake et al. | |
| 2012/0164624 A1 * | 6/2012 | Natan et al. | 435/5 |

FOREIGN PATENT DOCUMENTS

| | | |
|---|---|---|
| CN | 1475805 A | 2/2004 |
| CN | 1995052 A | 7/2007 |
| CN | 101082583 A | 12/2007 |

(Continued)

OTHER PUBLICATIONS

Kouassi et al. Analytical Chemistry 78: 3234-3241 (2006).*
Shen et al. Biophysical Chemistry 115: 63-66 (2005).*
Kong et al. Water Research 36: 2802-2812 (2002).*
Brasher et al. Current Microbiology 37: 101-107 (1998).*
Elnifro et al. Clinical Microbiology Reviews 13: 559-570 (2000).*
Helps et al. Journal of Clinical Microbiology 41: 2734-2736 (2003).*
Koch et al., "Uptake and Metabolism of a Dual Fluorochrome Tat-nanoparticle in HeLa Cells", Bioconjugate Chem., vol. 14, 2003, pp. 1115-1121.

(Continued)

*Primary Examiner* — Angela M Bertagna

(74) *Attorney, Agent, or Firm* — Birch, Stewart, Kolasch & Birch, LLP

(57) ABSTRACT

A method and kit for determining a nucleic acid is provided, including: providing magnetic nanoparticles and detectable nanoparticles to the sample, wherein the magnetic nanoparticles and detectable nanoparticles respectively contain oligonucleotides attached thereto, and the detectable nanoparticles contain at least one kind of nanoparticles with detectable signals distinct from the others, and the oligonucleotides attached on each kind of the detectable nanoparticles are complementary to a region of one of the nucleic acids in the sample; reacting the magnetic and detectable nanoparticles with the sample; and detecting signals from each kind of the detectable nanoparticles for determining the nucleic acid for each in the sample.

13 Claims, 4 Drawing Sheets

(56) References Cited

FOREIGN PATENT DOCUMENTS

| TW | 200738876 A | 10/2007 |
|---|---|---|
| TW | 201003070 A1 | 1/2010 |
| WO | WO 0242498 A2 * | 5/2002 |
| WO | WO 2006/131892 A2 | 12/2006 |

OTHER PUBLICATIONS

Alivisatos et al., "Organization of 'nanocrystal molecules' using DNA", Letters to Nature, vol. 382, Aug. 15, 1996, pp. 609-611.
Chen et al., "Nanoparticle Superstructures Made by Polymerase Chain Reaction: Collective Interactions of Nanoparticles and a New Principle for Chiral Materials", Nano Letters., vol. 9, No. 5, 2009, pp. 2153-2159 (published online Mar. 25, 2009).
Deng et al., "DNA-Encoded Self-Assembly of Gold Nanoparticles into One-Dimensional Arrays", Angew. Chem. Int. Ed., vol. 44, 2005, pp. 3582-3585.
Higashi et al., "Regulation of PCR efficiency with magnetic nanoparticles in a rotating magnetic field", Chemical Physics Letters, vol. 506, 2011, pp. 239-242 (published online Mar. 9, 2011).
Huang et al., "Size and Surface Effect of Gold Nanoparticles (AuNPs) in Nanogold-Assisted PCR", Surface Review and Letters, vol. 15, No. 6., 2008, pp. 757-762.
Li et al., "Nanoparticle PCR: Nanogold-Assisted PCR with Enhanced Specificity", Angew. Chem. Int. Ed., vol. 44, 2005, pp. 2-6.
Li et al., Enhancing the efficiency of a PCR using gold nanoparticles, Nucleic Acids Research, vol. 33, No. 21, 2005, pp. 1-10 (published online Nov. 27, 2005).
Loweth et al., "DNA-Based Assembly of Gold Nanocrystals", Angew. Chem. Int. Ed., vol. 38, No. 12, 1999, pp. 1808-1812.
Nicewarner-Pena et al., "Hybridization and Enzymatic Extension of Au Nanoparticle-Bound Oligonucleotides", J. Am. Chem. Soc., vol. 124, No. 25, 2002, pp. 7314-7323 (published online Jun. 1, 2002).
Strelau et al., "Detection of PCR products amplified from DNA of epizootic pathogens using magnetic nanoparticles and SERS", J. Raman Spectrosc., vol. 42, 2011, 243-250 (published online Jul. 20, 2010).
Su et al., "Composite Organic-Inorganic Nanoparticles (COINs) with Chemically Encoded Optical Signatures", Nano Letters, vol. 5, No. 1, 2005, pp. 49-54 (published online Dec. 8, 2004).
Tokareva et al., "Hybridization of Oligonucleotide-Modified Silver and Gold Nanoparticles in Aqueous Dispersions and on Gold Films", J. Am. Chem. Soc., vol. 126, No. 48, 2004, pp. 15784-15789 (published online Nov. 11, 2004).
Vu et al., "Gold Nanoparticle Effects in Polymerase Chain Reaction: Favoring of Smaller Products by Polymerase Adsorption", Anal. Chem., vol. 80, No. 14, Jul. 15, 2008, pp. 5462-5467 (published online Jun. 18, 2008).
Wan et al., "The effects of gold nanoparticles with different sizes on polymerase chain reaction efficiency", IOP Publishing, Nanotechnology, vol. 20, 2009, pp. 1-5 (published online Jul. 21, 2009).
Yang et al., "Evaluation of gold nanoparticles as the additive in real-time polymerase chain reaction with SYBR Green I dye", IOP Publishing, Nanotechnology, vol. 19, 2008, pp. 1-9 (published online May 14, 2008).
Zhao et al., "Asymmetric and symmetric PCR of gold nanoparticles: A pathway to scaled-up self-assembly with tunable chirality", J. Mater. Chem., vol. 22, 2012, pp. 5574-5580 (published online Feb. 9, 2012).
Chinese Office Action issued Nov. 15, 2014 for Chinese Application No. 201210574505.X.

* cited by examiner

US 9,512,468 B2

DETECTION METHOD USES MAGNETIC AND DETECTABLE NANOPARTICLES WITH OLIGONUCLEOTIDES ATTACHED THERETO

INCORPORATION BY REFERENCE OF SEQUENCE LISTING

A sequence listing submitted as a text file via EFS-Web is incorporated herein by reference. The text file containing the sequence listing is named "0965-A24125-US_Seq_Listing.txt"; its date of creation is Oct. 2, 2012; and its size is 4,096 bytes.

TECHNICAL FIELD

The technical field relates to method and kit for detection of nucleic acid.

BACKGROUND

The polymerase chain reaction (PCR) has been developed for several decades and is broadly used in nucleic acid analyses. Currently, real-time PCR has been rapidly taken by researchers because of its high sensitivity and the ability for quantitative analyses. The quantitative result of real-time PCRs is conducted by detecting fluorescent intensity from fluorescent dyes, like SYBR green (DreamTaq™), which bind to a target DNA or RNA. However, the fluorescent results are easily influenced by background noises and the dye degrades over time, resulting in limitations for detection. A method for improving the sensitivity and detection limits of PCR reactions is required.

SUMMARY

A detailed description is given in the following embodiments with reference to the accompanying drawings.

One embodiment of the invention provides a method for determining at least one kind of nucleic acids in a sample. The method comprises the following steps: providing magnetic nanoparticles and detectable nanoparticles to the sample; reacting the magnetic and detectable nanoparticles with the sample; and detecting signals from each kind of the detectable nanoparticles for determining the nucleic acid for each in the sample, in which the magnetic nanoparticles and detectable nanoparticles respectively comprise oligonucleotides attached thereto, and the detectable nanoparticles comprise at least one kind of nanoparticles with detectable signals distinct from the others, and the oligonucleotides attached on each kind of the detectable nanoparticles are complementary to a region of one of the nucleic acids in the sample.

Another embodiment of the invention provides a kit for determining a nucleic acid. The kit comprises a mix containing magnetic nanoparticles and detectable nanoparticles, in which the magnetic nanoparticle and the detectable nanoparticle respectively comprise oligonucleotides attached thereto.

BRIEF DESCRIPTION OF THE DRAWINGS

The invention can be more fully understood by reading the subsequent detailed description and examples with references made to the accompanying drawings, wherein.

DETAILED DESCRIPTION

Figure 1:
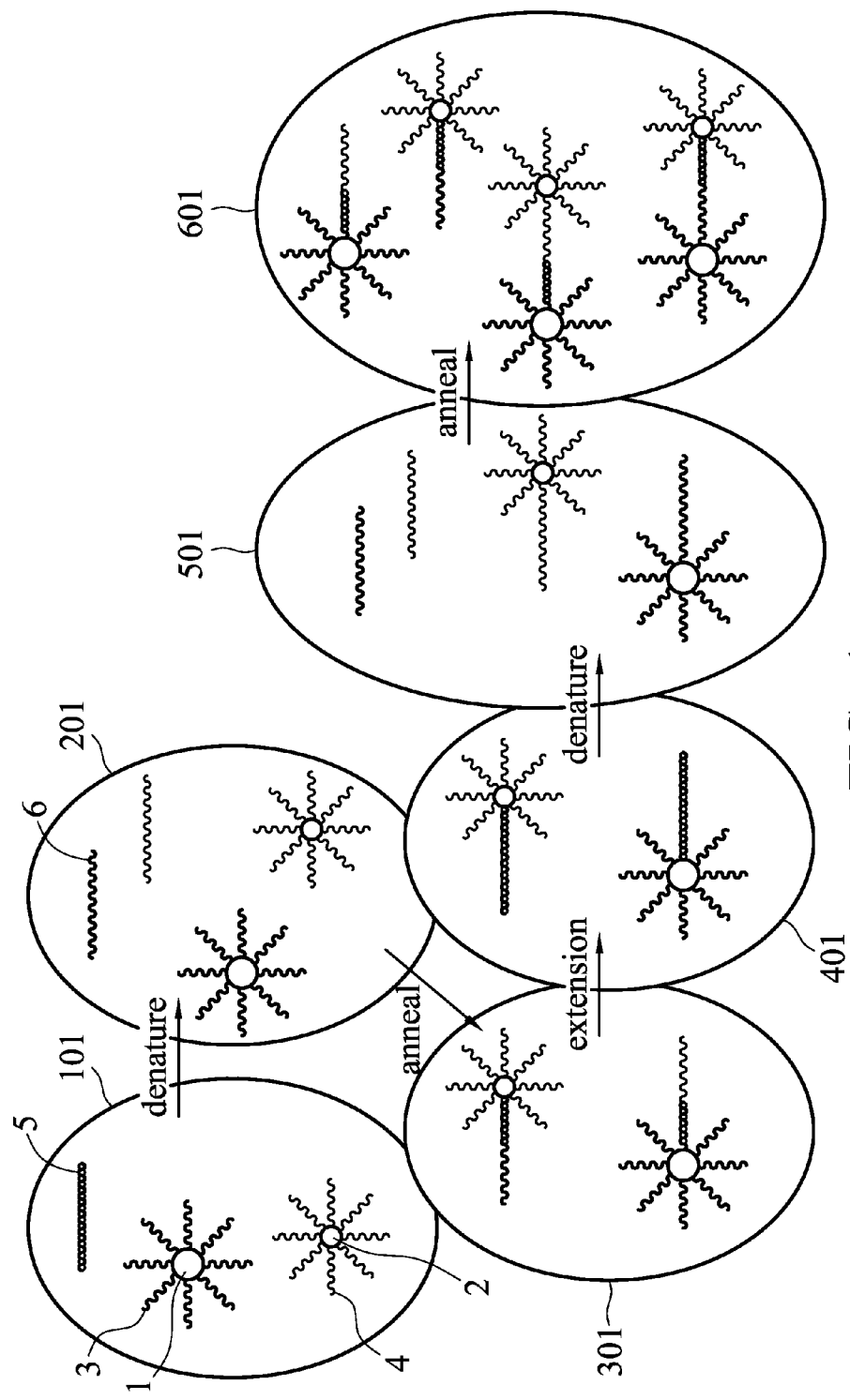
FIG. 1 is schematic diagram showing the reaction of the magnetic and detectable nanoparticles and the target nucleic acid in a PCR cycle according to an exemplary embodiment.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

One embodiment of the invention provides a method of determining a nucleic acid by using a nanoparticle-based system for a nucleic acid amplification reaction, and for example, for a polymerase chain reaction (PCR) or real-time PCR. The nanoparticle-based system comprises magnetic nanoparticles and detectable nanoparticles, in which two nanoparticles respectively comprise oligonucleotides attached thereto. The oligonucleotide on the magnetic nanoparticle is not complementary to that on the detectable nanoparticle so that the magnetic and detectable nanoparticles do not interact with each other under normal conditions. The oligonucleotides each are designed complementary to a region of the target nucleic acid, functioning like a nucleic acid primer which hybridizes to the target nucleic acid and is extended to form a sequence complementary to the target nucleic acid. Once extended, the two nanoparticles may form a complex by hybridizing the extended nucleotide sequences on the magnetic and detectable nanoparticles. The complex can be collected with a magnetic trapping technique, and the target nucleic acid can be determined according to the signals from the detectable nanoparticles and the nucleic acid amplification reaction cycle number.

One embodiment as shown in FIG. 1 is provided for example. A sample for detection (5) and the detectable nanoparticles (1) and magnetic nanoparticles (2) are dispersed in a PCR assay (Step 101). Oligonucleotides (3, 4) are attached onto the detectable nanoparticles (1) and magnetic nanoparticles (2) respectively, in which the oligonucleotides on the magnetic and detectable nanoparticles are designed as primers for the target nucleic acid (5). Noting that the oligonucleotides on the magnetic nanoparticle are not complementary to those on the detectable nanoparticles, the magnetic and detectable nanoparticles do not interact (hybridize) with each other. During the PCR reaction, the target nucleic acid is denatured to form single-stranded nucleic acids (6) (Step 201). As the denaturation process is finished, the single-stranded nucleic acids are annealed and hybridized to the oligonucleotides on the magnetic and detectable nanoparticles (Step 301). After, the oligonucleotides attached to the nanoparticles start to extend and form sequences complementary to the captured nucleic acid (Step 401). The PCR reaction undergoes a further denaturation process, separating the single-stranded nucleic acid and the synthesized nucleotide sequences attached on the nanoparticles (Step 501). The free nucleic acids and the nucleotide sequences attached on the nanoparticles are annealed through the crosslinking of the complementary sequences, forming, amongst other things, a complex (Step 601). The complex consists of the magnetic and detectable nanoparticles through the crosslinking of the extended nucleotide sequences. Thereafter, the complex not only can be magnetically trapped in a magnetic field but also be detected by signals from the detectable nanoparticles. The target nucleic acid can therefore be derived from the signals detected. The nucleic acid according to the invention may comprise single-stranded nucleic acids, double-stranded nucleic acids, or combinations thereof, such as DNAs, RNAs, or combinations thereof.

According to one embodiment of the invention, the detection limit of the nucleic acid amplification reaction can be dramatically reduced and the reaction time can be decreased as there would be no need for extended reaction cycles.

In another embodiment, the disclosure provides a method for determining at least one kind of nucleic acid in a sample by using more than one kind of the detectable nanoparticles each of which has a distinct and detectable signal. Specifically, the method comprises magnetic nanoparticles and detectable nanoparticles respectively with oligonucleotides attached thereon, as described above. The characteristics are that, the detectable nanoparticles comprise at least one kind of nanoparticle with detectable signals distinct from the others, and the oligonucleotides attached on each kind of the detectable nanoparticles are complementary to a region of one of the nucleic acids in the sample, functioning like primers for one of the target nucleic acids. The oligonucleotides on different magnetic and detectable nanoparticles are designed not to be complementary to each other so that the oligonucleotides on different nanoparticles do not interact with each other. As the detectable signals are from different detectable nanoparticles, each of the target nucleic acid can be determined in one single PCR reaction, thus simplifying the multiplexing process.

The magnetic nanoparticle recited herein refers to any nanoparticle with magnetism without specific limitations. The magnetic nanoparticle according to the invention may comprise iron-oxide nanoparticles (IONPs), superparamagnetic iron oxide nanoparticles (SPIONs), or the like, or combinations thereof. In one example, the magnetic nanoparticle can be surface modified, such as silicon oxide, dextran or the like, for stability, application or oligonucleotide attachment.

The detectable nanoparticle recited herein refers to any nanoparticle which can be chemically or electrochemically or optically detected, but it is not limited thereto. The detectable nanoparticle is preferably optically detectable, such as surface enhanced Raman scattering (SERS) active nanoparticles, fluorescent nanoparticles, quantum dots, or the like, or combinations thereof. The SERS-active nanoparticle can be commercially available or produced in a laboratory. It is well-known that SERS-active nanoparticles consist of metals, such as gold, silver, or the like, or alloys thereof. The surface of SERS-active nanoparticles may be modified for oligonucleotide attachment or application without specific limitations. The fluorescent nanoparticle recited herein refers to any nanoparticle which is capable of showing fluorescent signals. The fluorescent nanoparticle may comprise: fluorochromes, such as fluorescein isothiocyanate (FITC), Alexa Fluor dyes, Cyanine dyes (C2, Cy3 and Cy5); fluorescent proteins, such as phytochrome-based near-infra-red fluorescent protein (iRFP); bioluminescences, such as firefly luciferase (Fluc) or *Gaussia* luciferase (Gluc); or the like; or combination thereof, or quantum dots based on for example CdSe or ZnS. In the case of determining different nucleic acid sequences in a sample, SERS-active nanoparticles with distinct SERS-signals, fluorescent nanoparticles with different fluorescent signals or a combination of SERS-active nanoparticles and fluorescent nanoparticles all can be used. As the magnetic nanoparticle can be trapped in a magnetic field and the detectable nanoparticle can be detected under an optical detection system, the method according to the invention can reduce the readout time and the process of a nucleic acid amplification reaction, such as PCR and real-time PCR. In addition, because of the detectable nanoparticle, in particularly SERS-active nanoparticles, the detection limits for nucleic acids can be reduced to sub-attomole or zeptomole levels with less background noises.

The oligonucleotide recited herein refers to a short nucleotide sequence with fifty or less bases. The oligonucleotide according to the invention is complementary to a region of the target nucleic acid, as a primer for the target nucleic acid, especially in a PCR or real-time PCR reaction. The oligonucleotide can be designed and synthesized according to well-known procedures without specific limitations. In one example, the oligonucleotide attached on the detectable nanoparticle is a forward primer for the target nucleic acid and the oligonucleotide on the magnetic nanoparticle is a reverse primer for the target. But the method of the invention is not limited to the example. Oligonucleotides on different nanoparticles may function like forward or reverse primers. The attachment of the oligonucleotides on the magnetic and detectable nanoparticles may follow a conventional process, like a chemical coupling, biotin-streptavidin conjugation, or the like. There is no specific limitation. It should be noted that the oligonucleotides on different nanoparticles should not be complementary for each other preventing the oligonucleotides on the nanoparticles from interacting with each other and thus failing to hybridize or anneal to the target nucleic acid. In the case of determining several different nucleic acids, the oligonucleotides on different detectable nanoparticles are designed as different primers, each for specifically binding to the target nucleic acid sequences.

The method according to embodiment of the invention is undertaken in a nucleic acid amplification reaction such as a PCR reaction, like real-time PCR reaction. A nucleic acid amplification reaction process comprises three major steps, denaturation, annealing and extension, as a cycle, which is repeated several times (cycles). According to the method of the invention, the nucleic acid amplification reaction cycle number is 1~40 cycles, or 20~40 cycles, but it is not limited thereto.

The method according to embodiments of the invention may further comprise a step of collecting the nanoparticles. As magnetic nanoparticles form a complex with the detectable nanoparticles by crosslinking the complementary sequences, a magnetic trapping technique is able to collect the nanoparticles for signal detection. The magnetic trapping technique may comprise conventional magnetic separation methods, such as magnetic separation columns, plats or chip, or automatic collection.

According to another embodiments of the invention, the method is useful for pathogen detection, diseases diagnoses, water purity detection, food safety detection, companion diagnostics or the like. As a method for determining the microbial concentration of contaminated water and foods or determining a biomarker level in biosamples from a subject suspected of being pathogen infected or suffering from cancers or other diseases by determining specific nucleic acid concentrations. The detection of water purity, food safety, pathogens and diseases can be easily completed according to the method of the invention.

The invention also provides a kit for determining a nucleic acid. The kit may comprise a mix containing the magnetic and detectable nanoparticles with oligonucleotides attached thereto as described above. The kit may also comprise a solution for a nucleic acid amplification reaction, which contains polymerases, deoxynucleotides, buffers, or the like.

EXAMPLES

Preparation of SERS-Active Gold Nanoparticles

Gold nanoparticles (AuNPs) were synthesized following the citrate reduction method. In the citrate reduction method, small AuNPs particles were made first and used as seed particles to grow the final larger AuNPs. For the small seed particles, trisodium citrate (50 mg) was dissolved in distilled water (5 mL) to produce a 1% solution. This was added to a refluxing solution of hydrogen tetrachloroaurate (20 mg) in distilled water (50 mL). The resulting solution went through a color change from light yellow to deep red/purple. The heat was removed after refluxing for 30 min. The UV-Vis spectrum for the solution was recorded from 300 nm to 900 nm and showed the characteristic surface plasma resonance (SPR) peak at wavelength 517 nm. A TEM image analysis showed a nanoparticle diameter of 12 nm±1 nm.

Large AuNPs were synthesized by seed particle growth with citrate reduction. A hydrogen tetrachloroaurate solution (1 mL, 11 mmoldm$^{-3}$ solution) was added to distilled water (32 mL) and brought to reflux with a condenser fitted. The seed solution from the above small AuNP synthesis was added to this (1 mL) followed closely by trisodium citrate solution (0.34 mL of 1% solution). The solution started to change to a blue color after 30 sec and a red color after 1 min. After 10 min, the heat was removed and the solution allowed to cool with stirring. The UV-Vis spectrum for the solution was recorded from 300 nm to 900 nm and showed the characteristic SPR peak at wavelength 535 nm. TEM image analysis showed a diameter of 51 nm ±2 nm. The large AuNPs were mixed with 50 mg of 4-mercaptobenzoic acid (MBA) dissolved in 5 mL of ammonia (1 mol/dm$^3$).

The SERS spectra of the MBA-AuNPs was recorded using a desk-top system. The final solution (0.2 mL) was diluted with water (0.8 mL) and placed in the liquid sample holder. The holder held the sample so that the laser focus point fell in the centre of the solution. The laser exited a 105 micrometer diameter waveguide and passed through a collimation lens giving a beam width of 0.25 cm. The beam then passed through a lens with a focus length of 0.7 cm giving a spot diameter of 100 micrometer at its focus point. With this set-up, the laser effectively illuminated and collected a signal from a volume of 6.9 nL within the sample.

Preparation of Oligonucleotide-Coated AuNPs

The oligonucleotide sequence as set forth in SEQ ID NO. 2 with a C6-amino modification was used to coat the MBA-AuNPs by standard 1-ethyl-3-(3-dimethylaminopropyl) carbodiimide (EDC) coupling between the —COOH group on the MBA and —NH2 group on the end of the oligonucleotide sequence. The MBA-AuNPs (118 microliters) were mixed with 1 microliter of a freshly prepared EDC solution in water (7 mg mL-1). A DNA solution containing the oligonucleotide sequence (2 microliters of 100 pmol L-1) was added and the solution was left overnight with stirring then centrifuged and re-dispersed in 120 microliters of water. Care was taken when decanting the clear liquid from the AuNPs as these were readily re-dispersed. The product from the reaction was referred to as SERS-NPs.

Preparation of Iron-Oxide Nanoparticles

Iron-oxide nanoparticles (IONPs) were synthesized under an argon atmosphere. FeCl$_2$ (0.0345 moles), FeCl$_3$ (0.069 moles) and deionized water (150 mL) were combined in a reaction flask. NaOH (5 mol/dm$^3$) was added to adjust the pH of the mixture. The solution was subjected to continuous stirring during the reaction until the mixture became basic. A formed black precipitate was washed with deionized water and pH adjusted to below 5 with glacial acetic acid. Finally, H$_2$O$_2$ (10 vol %) was gradually added until no further reaction occurred. This was determined as being the point at which no further effervescence occurred on addition of fresh H2O2. The product was washed and dispersed in fresh deionized water and dextran (MW=10,000 Da) was then added. After ultrasonic mixing, NH$_4$OH was added to bring the pH to 10. The mixture was then continuously stirred while being heated to 75° C. and held at this temperature for 60 min. To remove excess dextran, the suspension was dialyzed using a membrane with a molecular weight cut-off (MWCO) of 10,000 Da. The suspension was then centrifuged at 6,000 rpm for 30 min to remove any large aggregate. Finally, the suspension was filtered through a 0.2 micrometer filter.

The IONPs were then coated with SiO$_2$. IONPs (5 mL, 3.6 mg mL$^{-1}$) were mixed in a 5 mL solution of water and 1 g of polyvinylpyrrolidone (PVP10). The PVP used had an average molecular weight of 10,000 Da. After 30 min, the IONPs were precipitated in ethanol and re-dispersed in 40 mL of distilled water. (3-Aminopropyl) triethoxysilane (APTES) (500 L) was then added followed by six drops of concentrated NH$_3$. After 30 min, the product was magnetically precipitated and washed with five consecutive acetone and water washes. The product was finally dispersed in water (2 mL). From TEM analysis, the IONPs showed a Fe$_3$O$_4$ core of 20 nm ±3 nm and a SiO$_2$ shell with thickness of 3 nm ±1 nm.

Preparation of Oligonucleotide-Coated IONPs

An oligonucleotide sequence as set forth in SEQ ID NO. 3 with C6-carboxy modification was used to coat the IONPs by standard 1-ethyl-3-(3-dimethylaminopropyl) carbodiimide (EDC) coupling between the —COOH group on the end of the oligonucleotide sequence and —NH$_2$ groups on the FeNPs. The FeNPs (118 microliters of 1 mg mL-1) were mixed with 1 microliter of a freshly prepared EDC (7 mg mL-1). A DNA solution containing the oligonucleotide sequence (2 microliters of 100 pmol L-1) was added to this and the solution was left overnight with stirring then magnetically precipitated and re-dispersed in 120 microliters of water. The sample was washed with 5-fold volume of water. The product from the reaction is referred to as MNPs.

PCR Assay with SYBR Green Detection

Figure 2:
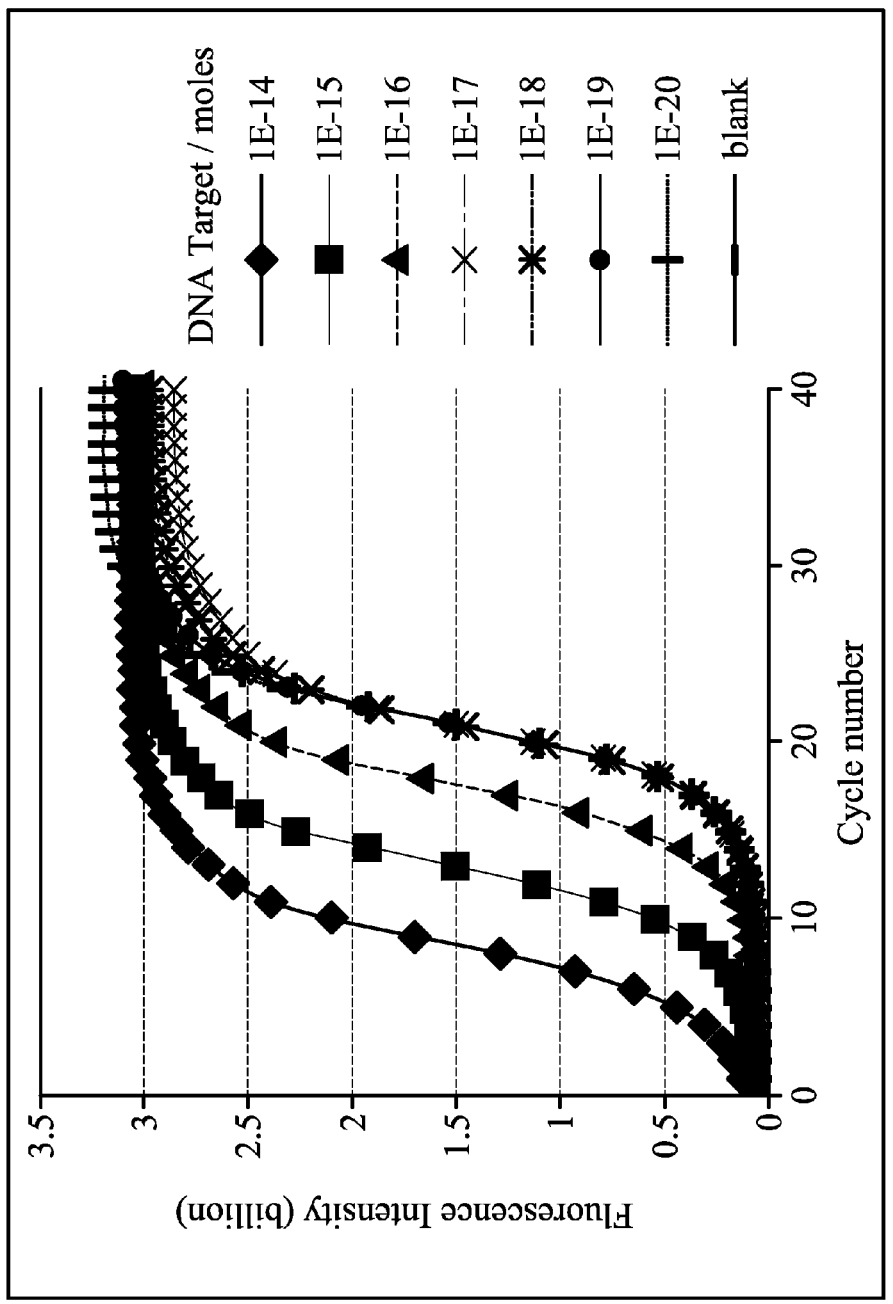
FIG. 2 is a diagram showing detection limits of a real-time PCR with SYBR Green detection according to an exemplary embodiment.

Real-time PCR analysis was performed using an Applied Biosystems 7500 Real-Time PCR system using SYBR Green detection (DreamTaq™ Green PCR Master Mix K1081). All synthetic DNA was purchased from Thermo-Fisher Scientific. The target DNA sequence as set for the in SEQ ID NO. 1 was an artificially synthetic, single stranded, 100-base-pair DNA from an *E. coli* plasmid for example *E. coli-K. pastoris* shuttle vector pPpHIS4. The primers were 44 base pairs long and consisted of a 20 base-pair thymine spacer at the 5' end and the 24 base pair active primer section as set forth in SEQ ID NOs. 2~3. Each analysis was run for 40 cycles using the following protocol: Pre-Heating at 95° C. for 10 min, Denaturing at 95° C. for 15 sec, and Annealing and Elongation at 60° C. for 60 seconds. The amount of DNAs in the reaction was 10 picomoles each for the primers. The amount of target DNAs varied from 10 femtomoles to 10 zeptomoles. The results from the real-time PCR analysis are shown in FIG. 2. It was shown that a decrease in the target DNA concentration from $1\times10^{-14}$ moles to $1\times10^{-17}$ moles in the reaction (total volume 24 ul) led to a quantifiable increase in the number of cycles required for the SYBR Green fluorescence to reach the threshold level. Any further decease in the target DNA level had no effect on the reaction. The time taken for the fluorescent signal to reach the threshold level for the $1\times10^{-17}$ moles down to $1\times10^{-20}$ moles was the same. For this reason, the quantifiable detection limit for the DNA assay performed using the SYBR Green detection (DreamTaq™ Green PCR Master Mix) was 10 attomoles.

PCR Assay with Nucleotide-Coated Nanoparticles Detection

Figure 3:
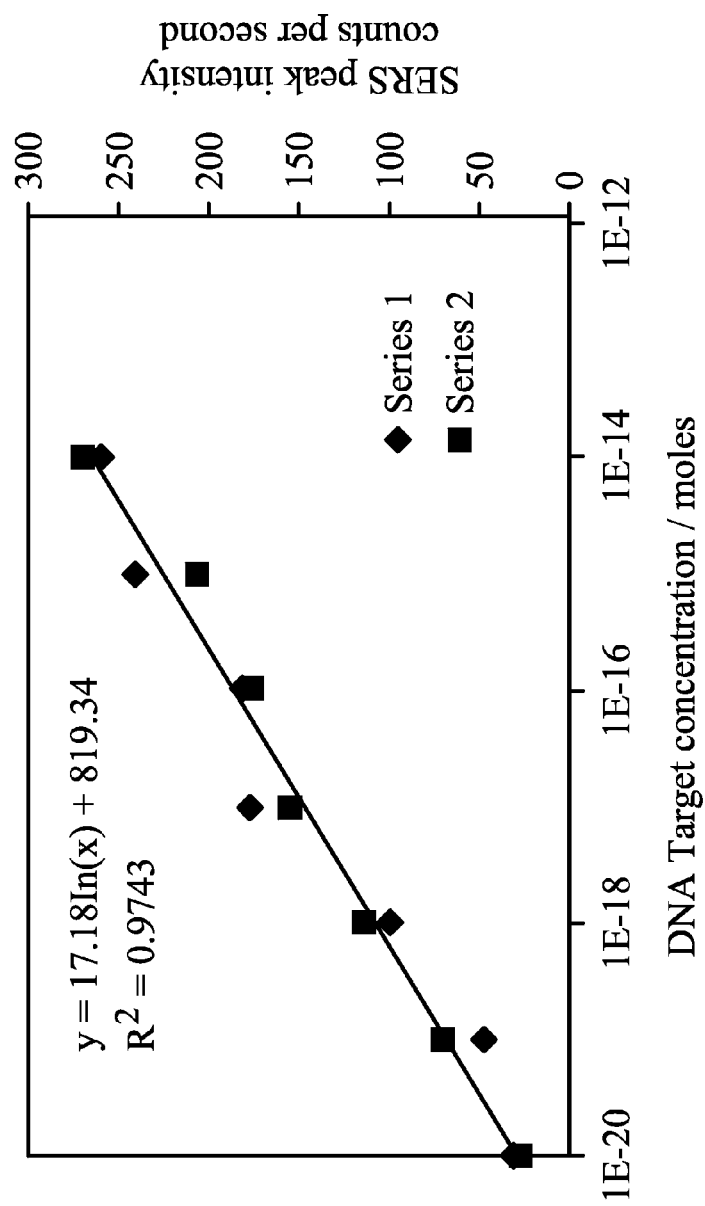
FIG. 3 is a diagram showing the SERS signal response for different nucleic acid concentrations by using oligonucleotide-attached nanoparticles in a PCR assay according to an exemplary embodiment.

For the SERS-based detection, the PCR primers were replaced with the primers coated on the nanoparticles. The primer coated on the SERS-NP was a reverse primer for the target DNA sequence and the primer coated on the MNPs was a forward primer for the target DNA sequence. The rest of the PCR protocol was left unchanged including the master mix and the cycling program. After 40 cycles, the samples were removed from the PCR device. The magnetic material was collected and washed several times with distilled water and finally acetone. During the washing steps, the SERS signal was recorded and showed a transition from the Raman signal dominated by SYBR Green in the initial PCR mix to a Raman signal dominated by the SERS-NPs. After washing, the SERS signal with intensity at 1077 $cm^{-1}$ was correlated with the initial target NA concentration. The results were shown in FIG. 3. The data showed a good correlation in the full range of the target DNA concentrations. The estimated detection limit with a 100 second integration time was around 1 zeptomole of the target DNA, based on a signal intensity of around 1000 and a noise level of 300.

Figure 4:
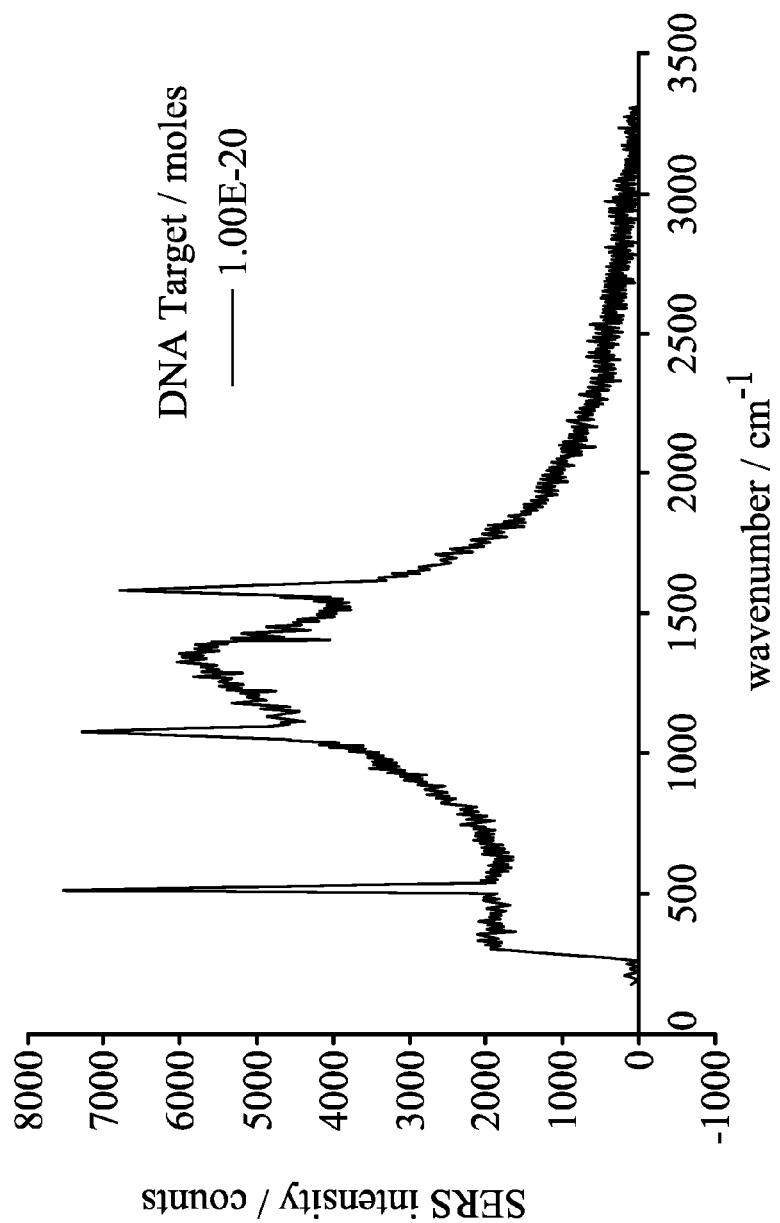
FIG. 4 is a SERS spectrum for 10 zeptomoles of the target DNA analyzed by oligonucleotide-attached nanoparticles in a PCR assay after 40 PCR cycles according to an exemplary embodiment.

In the performed test assay, a SERS signal was obtained from the 10 zeptomoles target DNA sample. This signal could be seen in FIG. 4. The signal height was at 1077 $cm^{-1}$ with 3000 counts and the noise level was ±100 counts. The peak at 516 $cm^{-1}$ was from the Si surface and may be a reference peak. From the signal to noise ratio in this sample, a detection limit of 1 zeptomole of nucleic acids could be estimated. For comparison, the standard PCR reaction based on fluorescence for the same system had a detection limit of 10 attomoles, 1000 times less sensitive.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for determining the presence of at least one nucleic acid in a sample, comprising:
providing magnetic nanoparticles and detectable nanoparticles to the sample, wherein the magnetic nanoparticles and detectable nanoparticles respectively comprise oligonucleotides attached thereto, and the detectable nanoparticles comprise at least one kind of nanoparticles with detectable signals distinct from the others, and the oligonucleotides attached on each kind of the detectable nanoparticles are complementary to a region of one of the nucleic acids in the sample;
reacting the magnetic and detectable nanoparticles with the sample to hybridize the oligonucleotides on the magnetic and detectable nanoparticles respectively to the nucleic acid and extend the oligonucleotides on the magnetic and detectable nanoparticles respectively to form complementary sequences of the nucleic acid; and
detecting signals from each kind of the detectable nanoparticles to determine the presence of the at least one nucleic acid in the sample,
wherein the detectable nanoparticles are SERS-active nanoparticles, and the SERS-active nanoparticles are gold nanoparticles with a diameter of 51 nm ±2 nm.

2. The method as claimed in claim 1, wherein the oligonucleotides on each of the magnetic and detectable nanoparticles are not complementary to each other.

3. The method as claimed in claim 1, wherein the magnetic nanoparticles comprise iron oxide nanoparticles, superparamagnetic iron oxide nanoparticles, or combinations thereof.

4. The method as claimed in claim 1, wherein the magnetic and detectable nanoparticles are reacted with the sample in a nucleic acid amplification reaction.

5. The method as claimed in claim 4, wherein the nucleic acid amplification reaction comprises a polymerase chain reaction (PCR) or real-time polymerase chain reaction (real-time PCR).

6. The method as claimed in claim 4, wherein the nucleic acid amplification reaction comprises 1~40 cycles.

7. The method as claimed in claim 1, further comprising a step of collecting the magnetic and detectable nanoparticles.

8. The method as claimed in claim 7, wherein the collection comprises a magnetic trapping technique.

9. A method for pathogen detection, comprising:
providing a sample for the pathogen detection, providing magnetic nanoparticles and detectable nanoparticles to the sample, wherein the magnetic nanoparticles and detectable nanoparticles respectively comprise oligonucleotides attached thereto, and the detectable nanoparticles comprise at least one kind of nanoparticles with detectable signals distinct from the others, and the oligonucleotides attached on each kind of the detectable nanoparticles are complementary to a region of target nucleic acids of the pathogen in the sample,
reacting the magnetic and detectable nanoparticles with the sample to hybridize the oligonucleotides on the magnetic and detectable nanoparticles respectively to the target nucleic acids and extend the oligonucleotides on the magnetic and detectable nanoparticles respectively to form complementary sequences of the target nucleic acids; and
detecting signals from each kind of the detectable nanoparticles to determine the target nucleic acids of the pathogen in the sample,
wherein the detectable nanoparticles are SERS-active nanoparticles, and the SERS-active nanoparticles are gold nanoparticles with a diameter of 51 nm ±2 nm.

10. A method for disease diagnosis, comprising:
providing a sample from a subject suffering the disease, providing magnetic nanoparticles and detectable nanoparticles to the sample, wherein the magnetic nanoparticles and detectable nanoparticles respectively comprise oligonucleotides attached thereto, and the detectable nanoparticles comprise at least one kind of nanoparticles with detectable signals distinct from the others, and the oligonucleotides attached on each kind of the detectable nanoparticles are complementary to a region of target nucleic acids of the disease in the sample,
reacting the magnetic and detectable nanoparticles with the sample to hybridize the oligonucleotides on the magnetic and detectable nanoparticles respectively to the target nucleic acids and extend the oligonucleotides on the magnetic and detectable nanoparticles respectively to form complementary sequences of the target nucleic acids; and
detecting signals from each kind of the detectable nanoparticles to determine the target nucleic acids of the disease in the sample,
wherein the detectable nanoparticles are SERS-active nanoparticles, and the SERS-active nanoparticles are gold nanoparticles with a diameter of 51 nm ±2 nm.

11. A method for water purity detection, comprising:
providing a sample for the water purity detection, providing magnetic nanoparticles and detectable nanoparticles to the sample, wherein the magnetic nanoparticles and detectable nanoparticles respectively comprise oligonucleotides attached thereto, and the detectable nanoparticles comprise at least one kind of nanoparticles with detectable signals distinct from the others, and the oligonucleotides attached on each kind of the detectable nanoparticles are complementary to a region of target nucleic acids of microbes in the sample,
reacting the magnetic and detectable nanoparticles with the sample to hybridize the oligonucleotides on the magnetic and detectable nanoparticles respectively to the target nucleic acids and extend the oligonucleotides on the magnetic and detectable nanoparticles respectively to form complementary sequences of the target nucleic acids; and
detecting signals from each kind of the detectable nanoparticles to determine the target nucleic acids of the microbes in the sample,
wherein the detectable nanoparticles are SERS-active nanoparticles, and the SERS-active nanoparticles are gold nanoparticles with a diameter of 51 nm ±2 nm.

12. A method for food safety detection, comprising:
providing a sample for the food safety detection, providing magnetic nanoparticles and detectable nanoparticles to the sample, wherein the magnetic nanoparticles and detectable nanoparticles respectively comprise oligonucleotides attached thereto, and the detectable nanoparticles comprise at least one kind of nanoparticles with detectable signals distinct from the others, and the oligonucleotides attached on each kind of the detectable nanoparticles are complementary to a region of target nucleic acids of microbes in the sample,
reacting the magnetic and detectable nanoparticles with the sample to hybridize the oligonucleotides on the magnetic and detectable nanoparticles respectively to the target nucleic acids and extend the oligonucleotides on the magnetic and detectable nanoparticles respectively to form complementary sequences of the nucleic acids; and detecting signals from each kind of the detectable nanoparticles to determine the target nucleic acids of the microbes in the sample, wherein the detectable nanoparticles are SERS-active nanoparticles, and the SERS-active nanoparticles are gold nanoparticles with a diameter of 51 nm ±2 nm.

13. A method for companion diagnostics, comprising:

providing a sample for companion diagnostics, providing magnetic nanoparticles and detectable nanoparticles to the sample, wherein the magnetic nanoparticles and detectable nanoparticles respectively comprise oligonucleotides attached thereto, and the detectable nanoparticles comprise at least one kind of nanoparticles with detectable signals distinct from the others, and the oligonucleotides attached on each kind of the detectable nanoparticles are complementary to a region of target nucleic acids for the companion diagnostics in the sample, reacting the magnetic and detectable nanoparticles with the sample to hybridize the oligonucleotides on the magnetic and detectable nanoparticles respectively to the nucleic acids and extend the oligonucleotides on the magnetic and detectable nanoparticles respectively to form complementary sequences of the target nucleic acids; and detecting signals from each kind of the detectable nanoparticles to determine the target nucleic acids for the companion diagnostics in the sample, wherein the detectable nanoparticles are SERS-active nanoparticles, and the SERS-active nanoparticles are gold nanoparticles with a diameter of 51 nm ±2 nm.

* * * * *

SEQUENCE LISTING

<160> NUMBER OF SEQ ID NOS: 3

<210> SEQ ID NO 1
<211> LENGTH: 100
<212> TYPE: DNA
<213> ORGANISM: Escherichia coli

<400> SEQUENCE: 1
ctgcggccaa cttacttctg acaacgatcg gaggaccgaa ggagctaacc gcttttttgc    60
acaacatggg ggatcatgta actcgccttg atcgttggga                         100

<210> SEQ ID NO 2
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 2
ctgcggccaa cttacttctg acaa                                          24

<210> SEQ ID NO 3
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 3
tcccaacgat caaggcgagt taca                                          24